ORNAMENTAL AND FRUITING PEACH TREE
Filed Nov. 16, 1951 2 SHEETS--SHEET 1
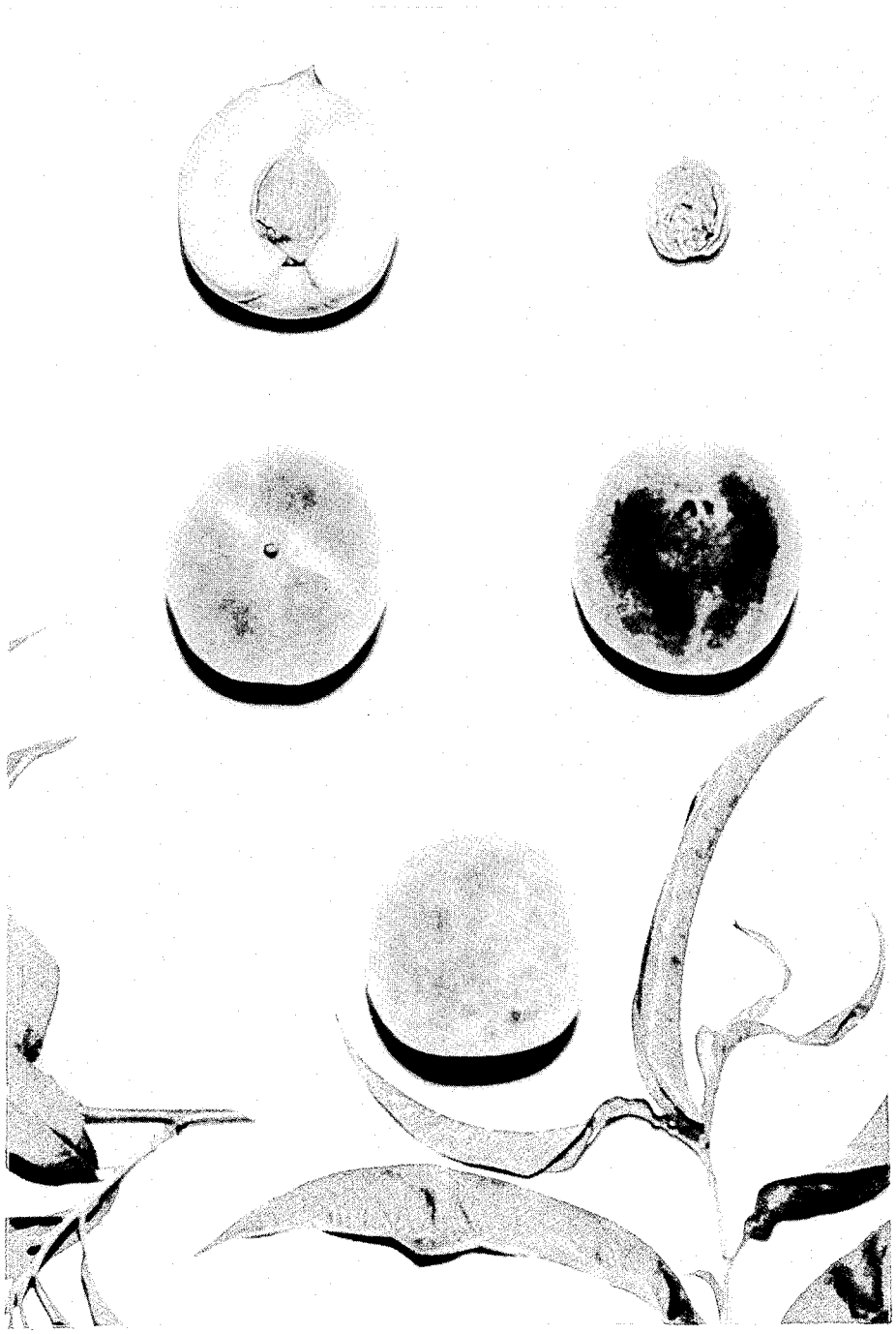
Inventor.
W. E. Lammerts
By: Robbins Cobb
Attorneys.

ORNAMENTAL AND FRUITING PEACH TREE
Filed Nov. 16, 1951 2 SHEETS--SHEET 2
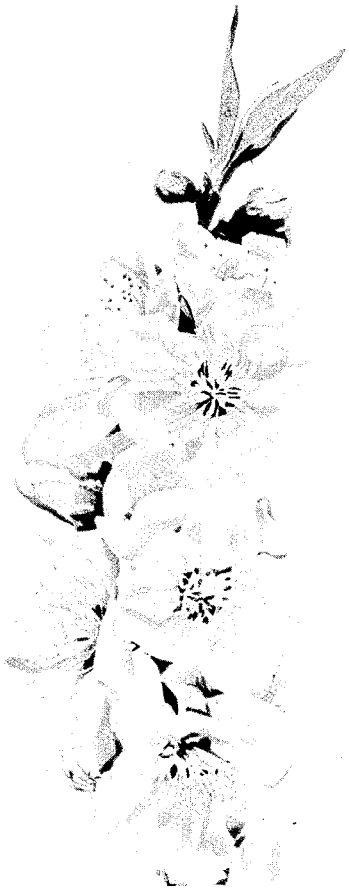
Inventor.
W. E. Lammerts
By: Robert Cobb
Attorneys Patented Dec. 23, 1952

Plant Pat. 1,156

UNITED STATES PATENT OFFICE 1,156

ORNAMENTAL AND FRUITING PEACH TREE

Walter E. Lammerts, La Canada, Calif., assignor to Descanso Distributors, Inc., La Canada, Calif., a corporation of California Application November 16, 1951, Serial No. 256,789

1 Claim. (Cl. 47—62)

The present invention relates to a new and distinct variety of peach tree which was originated by me by cross-pollinating two unnamed and unpatented peach seedlings respectively identified in my breeding and test records by the numbers 41064/19 and 40003/18, the former being the male parent and the latter the female parent.

The primary objective in making this cross was to produce a new and improved variety of peach tree especially suited for home use and which combines ornamental flowering qualities with abundant production of good quality fruit. This objective was fully achieved, as evidenced by the fact that the new variety resembles the variety "Robin" (Plant Patent No. 529) in respect to the coloration, general shape and appearance of the fruit, but having a more uniform scarlet-red color on fruit exposed to the sun, while significantly differing from "Robin" by its abundant production of very large, ornamental, single type flowers of Rhodamine Pink to China Rose color, as compared to the relatively smaller and less ornamental flowers of "Robin."

The tree of my new variety is much more vigorous than "Robin" and has a significantly shorter chilling requirement. Accordingly, following warm winters, my new variety leafs out and begins flowering by the middle of January in the west coast region, and is in full flower by the last week in January, whereas the variety "Robin" characteristically does not begin flowering until late February or early March, even following warm winters. Colder winters may delay the leafing and flowering of my new variety until late February or early March, but it is especially well-adapted to warm winter climatic areas.

Asexual reproduction of this new variety by budding at La Canada, California, shows that the foregoing characteristics come true to form and are established and transmitted through succeeding propagations.

The accompanying drawings show specimens of the flowers, fruit and foliage of the new variety, the fruit being shown in both elevation and in plan, as well as in section without the stone, and the stone being shown separately in elevation.

The following is a detailed description of the new variety, based upon observations of specimens grown at La Canada, California, with color terminology in accordance with British Royal Horticultural Color Standards, except where general color terms of ordinary dictionary significance are obvious:

Dates first and last picking: June 8th to 15th in warm spring; June 25th to July 1st, in cool, foggy spring.

Tree: Large; vigorous; upright; open; vase formed; very productive; regular bearer.

*Trunk.* — Medium stockiness; medium smoothness.

*Branches.* — Medium stockiness; medium smoothness. Color—lower surface—near Lettuce Green, Plate 861/1; upper surface—near Garnet Brown, Plate 918/3.

*Leaves.* — Length — 4¼ to 8¾ inches. Width—1 to 2 inches. Large; acuminate; lanceolate; medium thickness. Color—near Spinach Green, Plate 0960; mid-rib strongly tinged with anthocyanin pigment especially in fall; many leaves strongly colored anthocyanin in late fall. Margin — finely serrate. Petiole — medium length; about ½ inch long; medium thickness. Glands—average number—1 or 2. Opposite; small; globose. Color—Green. Position—immediately below leaf blade at upper part of petiole. Stipules—very small; practically absent.

Flower buds: Large; long; obtuse; free; slightly pubescent.

Flowers: Dates first and full bloom—following warm winter—January 20th; full bloom January 30th. Following colder winter—February 8th; full bloom March 9th. Early compared with other varieties.

*Size.*—Large; 1¾ inches in diameter.

*Color.*—Rhodamine Pink, Plate 527/2 veins, turning very slightly to Plate 527/1; older flower petal veins turn to China Rose, Plate 024/1; claw turns to China Rose, Plate 024; margins turn lighter to Rhodamine Pink, Plate 527/3; flower generally as it ages becomes a rather uniform China Rose, Plate 024/1, with small margins of Rhodamine Pink, Plate 527/3.

*Fruit*

Maturity when described: Hard ripe. Date, June 20th.

*Size.*—Medium. Diameter—axial—2 to 2¼ inches. Transverse in suture plane—2¼ to 2⅜ inches. Transverse at right angles to suture plane—2¼ to 2⅜ inches.

*Form.*—Uniform; symmetrical; globose to broadly ovoid.

*Suture.*—Distinct but shallow; extends from base to apex; has slight depression beyond pistil point.

*Ventral surface.*—Slightly lipped toward base. Lips—equal to slightly unequal.

*Cavity.*—Rounded; elongated in suture plane with suture showing on one side. Depth—⅜ to ½ inch. Breadth—¾ inch. Length—1 inch.

*Base.*—Rounded.

*Apex.*—Rounded. Pistil point—oblique.

*Stem.*—Length—¼ inch. Medium thickness; glabrous. Adherence to stone—medium strength.

*Skin.*—Medium thickness; medium tenderness; free. Tendency to crack—none in dry season. Color—Sap Green, Plate 62/2, at base, to Uranium Green, Plate 63/2, stippled with Scarlet, Plate 19/1 on cheeks; near apex and on cheeks exposed to sun Scarlet, Plate 19/1, striped and speckled with Currant Red, Plate 821/3, to Oxblood Red, Plate 00823/3, at apex.

*Flesh.*—Color—white with greenish tinge toward pit; streaked with red next to skin and red streaks in flesh under apex. Surface of pit cavity — greenish white. Amygadalin — scant. Juice — abundant; watery. Texture—firm to medium soft when fully ripe; fine; melting. Fibres—few; fine. Ripens—even, except in cool weather when flesh around pit remains green. Aroma—pronounced. Eating quality—good.

*Stone.*—Semi-cling; adheres to flesh over entire surface when completely ripe; some fruits are fully freestone except for short fibres along ridges. Fibres—short. Size—medium. Length — 1 to 1¼ inches.

Breadth—⅞ to 1 inch. Thickness—¾ to ⅞ inch. Form—elliptical; apex pointed. Base—oblique. Hilum—narrow; oblong. Apex—acute. Sides—unequal; curved on right and left sides. Surface—irregularly furrowed throughout; ridged throughout; pitted throughout. Ridges—jagged toward base. Pits—circular and elongated. Ventral edge—thin without wing. Dorsal edge—narrow with narrow grooves toward base. Color of stone—near Maize Yellow, Plate 607/3.

Use: Market, local and dessert.

Keeping quality: Medium.

Shipping quality: Medium.

I claim:

A new and distinct variety of peach tree of the combined ornamental and fruiting class, substantially as herein shown and described, particularly characterized as to novelty by the resemblance of its fruit to that of the variety "Robin" (Plant Patent No. 529) in respect to its coloration, general shape and appearance, but having a more uniform scarlet-red color on the fruit exposed to the sun, while dominantly differing from "Robin" by its abundant production of very large, ornamental, single type flowers of Rhodamine Pink to China Rose color, by its more vigorous habit of growth, and by its shorter chilling requirement that is especially adapted to warm winter climates, with consequent earlier leafing and flowering habits than "Robin."

WALTER E. LAMMERTS.

No references cited.